(12) United States Patent
Terrasse et al.

(10) Patent No.: US 10,099,006 B2
(45) Date of Patent: Oct. 16, 2018

(54) ASSEMBLY FOR INJECTING A VISCOUS LIQUID PRODUCT

(71) Applicant: MEDEX, Saint-priest (FR)

(72) Inventors: Samuel Terrasse, Saint Alban de Roche (FR); Damien Matray, Bourgoin-jallieu (FR); Nathalie Maneuf, Jardin (FR); Anne-Marie Milcent, Lyons (FR)

(73) Assignee: MEDEX, Saint-Priest (FR)

( * ) Notice: Subject to any disclaimer, the term of this patent is extended or adjusted under 35 U.S.C. 154(b) by 94 days.

(21) Appl. No.: 14/406,962

(22) PCT Filed: Jun. 13, 2013

(86) PCT No.: PCT/EP2013/062238
§ 371 (c)(1),
(2) Date: Dec. 10, 2014

(87) PCT Pub. No.: WO2013/186300
PCT Pub. Date: Dec. 19, 2013

(65) Prior Publication Data
US 2015/0224248 A1    Aug. 13, 2015

Related U.S. Application Data

(60) Provisional application No. 61/659,288, filed on Jun. 13, 2012.

(30) Foreign Application Priority Data

Jun. 13, 2012    (FR) ..................... 12 55530

(51) Int. Cl.
*A61M 5/148*    (2006.01)
*A61M 5/00*    (2006.01)
(Continued)

(52) U.S. Cl.
CPC .......... *A61M 5/1483* (2013.01); *A61M 5/007* (2013.01); *A61M 39/00* (2013.01);
(Continued)

(58) Field of Classification Search
CPC ...... A61M 2039/0009; A61M 2205/18; A61M 2205/3334; A61M 2209/045;
(Continued)

(56) References Cited

U.S. PATENT DOCUMENTS 3,628,813 A * 12/1971 Lee, Jr. ............... A61M 1/3653
285/120.1
3,888,239 A    6/1975 Rubinstein
(Continued)

FOREIGN PATENT DOCUMENTS

EP    0 648 513 A1    4/1995
EP    0648513 A1 *    4/1995 ............ A61M 39/24
(Continued)

OTHER PUBLICATIONS

Machine translation of EP 0648513 A1.*
(Continued)

*Primary Examiner* — Emily Schmidt
(74) *Attorney, Agent, or Firm* — Marsh Fischmann & Breyfogle LLP

(57) ABSTRACT

An assembly used in the injection of a contrast product into a patient is disclosed. This assembly includes a container, an injection flowpath, and a filling flowpath. The injection flowpath extends from the container to the patient, while the filling flowpath extends from a feed source to the container. Part of the injection flowpath is also used by the filling flowpath. One connector is disposed between an upstream filling line tubular section and a pump coupling section within the filling flowpath, while another connector is disposed between a downstream filling line tubular section and
(Continued)

this same pump coupling section. This allows the upstream filling line tubular section, the pump coupling section, and the downstream filling line tubular section to differ in one or more respects, for instance with regard to hardness.

13 Claims, 1 Drawing Sheet

(51) Int. Cl.
*A61M 39/24* (2006.01)
*A61M 39/00* (2006.01)

(52) U.S. Cl.
CPC ..... *A61M 39/24* (2013.01); *A61M 2039/0009* (2013.01); *A61M 2205/18* (2013.01); *A61M 2205/3334* (2013.01); *A61M 2209/045* (2013.01)

(58) Field of Classification Search
CPC ...... A61M 39/00; A61M 39/24; A61M 5/007; A61M 5/1483; A61M 2005/3128; A61M 5/168; A61M 5/1486; A61M 5/152; A61M 5/148; A61M 2005/14553
See application file for complete search history.

(56) References Cited

U.S. PATENT DOCUMENTS

| | | | |
|---|---|---|---|
| 3,895,741 A | | 7/1975 | Nugent |
| 4,280,637 A | * | 7/1981 | Runciman ............. A61M 5/148 222/105 |
| 4,596,575 A | | 6/1986 | Rosenberg et al. |
| 5,078,683 A | | 1/1992 | Sancoff et al. |
| 5,165,874 A | * | 11/1992 | Sancoff ............. A61M 5/14228 128/DIG. 12 |
| 5,348,539 A | | 9/1994 | Herskowitz |
| 5,355,024 A | | 10/1994 | Elliott et al. |
| 6,355,024 B1 | * | 3/2002 | Small ..................... A61J 3/002 604/500 |
| 8,628,514 B2 | | 1/2014 | Fago |
| 8,747,356 B2 | | 6/2014 | Cocker et al. |
| 2006/0167404 A1 | * | 7/2006 | Pirovano ............... A61M 5/152 604/65 |
| 2008/0275590 A1 | | 11/2008 | Ross |
| 2010/0249586 A1 | * | 9/2010 | Cocker ............. A61M 5/14546 600/432 |
| 2010/0286512 A1 | * | 11/2010 | Dhawale ................. G01T 1/00 600/431 |
| 2011/0196304 A1 | | 8/2011 | Kramer et al. |
| 2011/0301539 A1 | | 12/2011 | Rickard |
| 2012/0046546 A1 | | 2/2012 | Strobl |

FOREIGN PATENT DOCUMENTS

| | | | | |
|---|---|---|---|---|
| EP | 0 650 739 A1 | | 5/1995 | |
| EP | 0676214 A1 | * | 10/1995 | .......... A61M 5/1486 |
| FR | 2 850 027 A1 | | 7/2004 | |
| FR | 2 991 881 A1 | | 12/2013 | |
| WO | 9632887 | | 10/1996 | |
| WO | WO 99/21600 A2 | | 5/1999 | |
| WO | 2003039433 A1 | | 5/2003 | |
| WO | WO 2004/067054 A2 | | 8/2004 | |
| WO | 2005072666 A1 | | 8/2005 | |
| WO | 2010117919 | | 10/2010 | |

OTHER PUBLICATIONS

Machine translation of EP 0676214 A1.*
International Search Report and Written Opinion of the International Searching Authority (Forms PCT/ISA/210 and PCT/ISA/237), dated Feb. 4, 2014, for International Application No. PCT/EP2013/062238.

\* cited by examiner

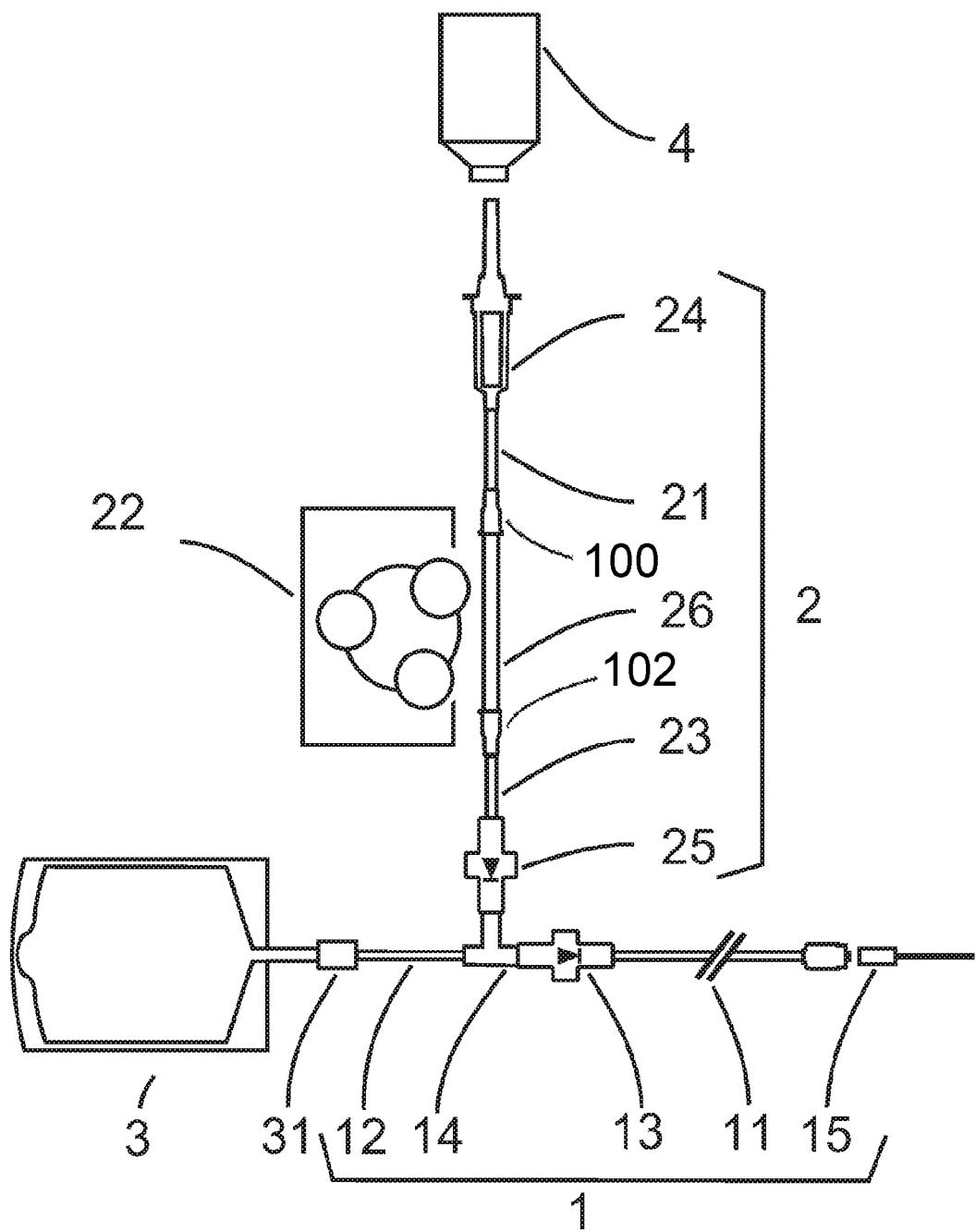

ASSEMBLY FOR INJECTING A VISCOUS LIQUID PRODUCT

CROSS REFERENCE TO RELATED APPLICATIONS

This application is the National Phase of PCT International Application No. PCT/EP2013/062238, filed on Jun. 13, 2013, which claims priority under 35 U.S.C. 119(e) to U.S. Provisional Application No. 61/659,288, filed on Jun. 13, 2012 and under 35 U.S.C. 119(a) to Patent Application No. 1255530, filed in France on Jun. 13, 2012, all of which are hereby expressly incorporated by reference into the present application.

TECHNICAL FIELD

The present invention relates to the general technical field of the administration of product, notably liquid or viscous, to a patient, for example by parenteral pathway, possibly from a flexible pocket.

More specifically, the present invention relates to an assembly for medical use allowing for the injection of liquid or viscous product into the human body.

OVERVIEW OF THE PRIOR ART

Advances in medicine have led to the development of different methods for analysis and monitoring the condition of patients.

Among these methods, there are the analyses made after the injection of a contrast product, for example for medical imaging which equally covers X-ray imaging, magnetic resonance imaging (MRI) and nuclear medicine.

In most cases, the contrast product injection operation requires the transfer of the contrast product between a container containing this contrast product and the patient. This transfer is implemented by using an assembly for medical use comprising an injection line—such as a tube connected to the container on the one hand and to the patient on the other hand—for the transfer of the contrast product between the container and the patient.

It is often necessary to fill the contrast product container prior to the transfer thereof to the patient. In this case, the injection operation comprises:
  a step of filling the container with the contrast product from the feed source, and
  a step of transferring the contrast product between the container and the patient.

To fill the container, a standalone device that makes is possible to fill the container from a feed source is, for example, used.

However, such a solution presents the drawback of requiring a large number of operations for:
  connecting/disconnecting the container to and from the standalone device on the one hand, and
  connecting/disconnecting the container to and from the injection line on the other hand.

These operations can reduce asepsis quality.

To remedy this drawback, EP 0 648 513 proposes an assembly for medical use comprising:
  an injection line for the transfer of the product to be injected between the container and the patient, and
  a filling line for the transfer of the product to be injected between a feed source and the container.

This assembly offers the advantage of limiting the number of connections/disconnections needed to implement the container filling step.

By using the assembly for medical use described in EP 0 648 513, the filling step can be implemented by three different techniques:
i) filling by gravity from the feed source:
  one drawback with this technique is that the time to fill the container is very long, which results in a very lengthy injection operation. The aim of the following two filling techniques is to reduce the filling time:
ii) filling by suction of the product contained in the feed source:
  one drawback with this technique is that it can degrade the quality of the contrast product. This is because, when filling by suction, notably using a syringe, a significant depression is created in the filling line and the water that makes up the contrast product can change to gaseous phase. This phenomenon is amplified in the case where the contrast product is heated. Another drawback with this technique relates to the head losses in the filling line. In effect, since the displacement of the contrast product is induced by the depression created by the syringe, the rate of displacement of the contrast product is limited by the pressure difference generated between atmospheric pressure and the pressure in the syringe, i.e. a physical limit of one bar;
iii) filling by pressurizing the feed source:
  one drawback with this technique is that it can be implemented only with a rigid feed source. Moreover, this technique can be implemented only at a very low pressure (less than one bar) in order to limit the risks of leaks. Finally, this technique does not make it possible to determine the quantity of product transferred between the primary source and the container.

One aim of the present invention is to propose an assembly for medical use that makes it possible to mitigate at least one of the abovementioned drawbacks.

PRESENTATION OF THE INVENTION

To this end, the invention proposes an assembly for medical use for injecting a patient with a liquid or viscous product, such as a contrast product, characterized in that the assembly comprises:
  an injection line for the transfer of the product to be injected between a container and the patient, said injection line comprising an upstream tubular part, a downstream tubular part and a thresholded non-return valve on the downstream tubular part, said thresholded non-return value allowing the liquid product to pass from the container to the patient,
  a filling line for the transfer of the product to be injected between a feed source and the container via the upstream tubular part, said filling line being connected to the injection line between the upstream and downstream tubular parts and comprising a non-return valve allowing the liquid product to pass from the feed source to the container,
  a coupling interface on the filling line intended to be coupled to a pumping unit allowing for the displacement of the liquid between the feed source and the container.

Preferred but nonlimiting aspects of the assembly for medical use according to the invention are as follows:
  the filling line comprises a nozzle upstream of the coupling interface and a nozzle downstream of the coupling interface, the hardness of the nozzle upstream of the coupling interface being greater than the hardness of the nozzle downstream of the coupling interface;

the hardness of the nozzle upstream of the coupling interface is equal to or greater than 70 ShA (the Shore hardness, expressed as Shore A or ShA, corresponds to a unit of measurement of the hardness of elastomers or of certain plastic materials very well known to those skilled in the art and recognized by the international standards ISO 868 and 7619, ASTM D 2240 and DIN 53505);

the filling line comprises a nozzle upstream of the coupling interface and a nozzle downstream of the coupling interface, the internal diameter of the nozzle upstream of the coupling interface being greater than the internal diameter of the downstream tubular part of the injection line;

the internal diameter of the nozzle upstream of the coupling interface is between 3 and 6 millimeters;

the filling line comprises a nozzle upstream of the coupling interface and a nozzle downstream of the coupling interface, the hardness of the nozzle downstream of the pumping unit being less than the hardness of the downstream tubular part of the injection line;

the Shore hardness of the nozzle downstream of the pumping unit is between 60 and 80 ShA;

the filling line comprises a nozzle upstream of the coupling interface and a nozzle downstream of the coupling interface, the diameter of the nozzle downstream of the coupling interface being greater than the diameter of the downstream tubular part of the injection line;

the assembly for medical use further comprises the container, said container being connected to the injection line prior to its use;

the container is a pocket made up to two sheets of material superposed and welded at their periphery to define a space intended to contain the liquid or viscous product;

the assembly for medical use further comprises a non-removable connection between the container and the injection line.

The reader will appreciate that the assembly for medical use can be used in an injector of the type described in the French patent application No. FR 1255530 filed in the name of the company MEDEX. In this case, the container of the assembly for medical use is a pocket comprising sheets superposed and welded at their periphery and a pipe for the passage of liquid or viscous product. This pocket is intended to be positioned in the injector in such a way that the pipe from the pocket constitutes the element of the pocket furthest away from the ground, so that any volume of air contained in the pocket is in contact with the pipe when the pocket is filled with liquid or viscous product.

PRESENTATION OF THE FIGURES

Other features and advantages of the invention will re-emerge from the following description, which is purely illustrative and nonlimiting and should be read in light of FIG. 1 which illustrates an embodiment of an assembly for medical use for injecting a liquid or viscous product into a patient.

DESCRIPTION OF EMBODIMENTS OF THE INVENTION

As indicated previously, an injection operation generally comprises two phases:

a phase of filling a container with a product to be injected, and a phase of administering the product to the patient from the container.

In effect, the container used in an injection operation is generally empty to allow the user to use it with different types and/or concentrations of products to be injected.

The injection assembly for medical use described below makes it possible to implement these two phases (i.e. filling/administration) during an injection operation.

General Information

With reference to FIG. 1, an embodiment of the assembly for medical use for injecting a patient with a liquid or viscous product, such as a contrast product, is illustrated.

The assembly for medical use comprises an injection line 1 and a filling line 2. The injection line 1 allows for the transfer of the product to be injected between a container 3 and the patient. The filling line 2 allows for the transfer of the product to be injected between a primary feed source 4 and the container 3.

The presence of a filling line 2 makes it possible to enhance the asepsis of the injection operation, the number of connections/disconnections needed to allow the container 3 to be filled being limited.

The assembly for medical use also comprises a pump coupling interface or pump coupling section 26 on the filling line 2. This coupling interface 26 makes it possible to couple a pumping unit 22 to the filling line 2 of the assembly for medical use.

The presence of a coupling interface 26, when associated with a pumping unit 22, makes it possible to speed up the rate of filling while limiting the risks of degrading the quality of the liquid product displaced between the primary feed source 4 and the container 3.

The pumping unit 22 can be a peristaltic pump—consisting of rollers and a motor—and the coupling interface 26 can be a flexible pipe intended to come into contact with the rollers of the peristaltic pump. The diameter, the thickness and the elasticity of the flexible pipe are adapted to make it possible to improve the coupling of the filling line 2 with the pumping unit 22. In particular, the pumping interface can be a pipe:

with an internal diameter of between 2 and 8 millimeters, preferentially between 3 and 6 millimeters and more preferentially equal to 4.8 millimeters, with a thickness of between 1 and 3 millimeters, preferentially between 1 and 2 millimeters and more preferentially equal to 1.6 millimeters, and with a Shore A hardness of between 55 and 75 ShA, preferentially between 55 and 65 ShA and more preferentially equal to 60 ShA.

The presence of a coupling interface 26 incorporated in the filling line 2 makes it possible to avoid any direct contact between the pumping unit 22 and the injectable solution.

Thus, it is no longer necessary to clean the pumping unit 22 each time the feed source is replaced, and notably when the feed sources used in succession contain products of different natures.

The asepsis of the filling operation is also improved, since the pumping unit 22 is not directly connected to the assembly for medical use, but is coupled thereto via the coupling interface 26.

Injection Line

The injection line 1 comprises an upstream tubular part 12, a downstream tubular part 11 and a connector 14 with three inlets—notably of Y or T connector type—between the upstream and downstream tubular parts 11, 12. The connector 14 with three inlets makes it possible to link the filling line 2 to the injection line 1.

One of ends of the injection line 1 comprises a coupling element—such as a "luer lock"—intended to be connected to an injection pipe 15. This injection pipe 15 is, for example, a catheter, a hypodermic or intravenous needle or any other type of injection pipe known to those skilled in the art.

The other end of the injection line 1 is connected to the container 3 intended to contain the product to be injected into the patient.

Advantageously, the container 3 can be incorporated in the assembly for medical use. In other words, the assembly for medical use comprises the container 3. In this case, the container 3 is preconnected to the injection line 1 during the manufacture of the assembly for medical use.

Thus, the user does not need to connect the container 3 to the injection line 1 when using the assembly for medical use.

This makes is possible to limit the number of operations necessary to install the assembly for medical use. This also makes it possible to increase the asepsis of the assembly for medical use. Finally, this makes it possible to limit the risks of error, for example linked to the connection of a container not matched to the assembly for medical use—when installing the assembly for medical use.

Preferably, the assembly for medical use further comprises a non-removable connection 31 between the container 3 and the injection line 1. This makes it possible to limit the risks of disconnection between the container 3 and the injection line 1.

In the context of the present invention, "non-removable connection" should be understood to mean an element (for example a weld, a bonding, or any other element known to those skilled in the art) allowing for a permanent joining of two parts such that these two parts can no longer be separated from one another, the joining of the two parts by this element being performed prior to use of the assembly, notably during the manufacture of the assembly.

In all cases, the container 3 intended to contain the product to be injected can be:
- a syringe consisting of a cylindrical body housing a piston covered by an elastomer seal on its front face, said piston being able to be displaced in translation between a retracted position (in which the syringe is empty) and a deployed position (in which the syringe is filled with product to be injected),
- a flexible pocket consisting, for example, of two sheets superposed and welded at their periphery to define a space intended to contain the liquid or viscous product,
- or any other type of container known to those skilled in the art.

However, in some embodiments, preference will be given to a container 3 of pocket type, notably to improve the asepsis of the assembly for medical use. In effect, in the case of a container 3 of syringe type, the inner portion of the cylindrical body situated behind the elastomer seal is in contact with the ambient air, which, upon displacements of the piston between the deployed and retracted positions, can reduce the asepsis.

The injection line 1 can also comprise a non-return valve 13 on the downstream tubular part 11. This non-return valve 13 allows the liquid to pass in a single direction, namely from the container 3 to the patient.

Advantageously, the non-return valve 13 can have a high opening threshold (i.e. greater than 500 mbar). This makes it possible to avoid the risks of transfer of liquid product directly to the patient (without passing through the container) during the filling phase.

The non-return valve 13 can also have a higher opening threshold, notably greater than 1.5 bar (ideally greater than or equal to 2 bar) to allow the assembly for medical use to be used in an injector of the type described in the French patent application No. FR 1255530 in the name of the company MEDEX.

Such an injector comprises a housing made up of two half-shells articulated in order to allow the relative displacement of the half-shells relative to one another between:
- an opened position for the placement of the container 3 of the assembly for medical use, and
- a closed position for the implementation of the filling and administration phases.

One of the half-shells comprises a deformable bladder—called "active bladder"—with variable volume under the action of a hydraulic power source feeding said bladder with hydraulic fluid. The other half-shell comprises a deformable cushion with constant volume—called "passive cushion".

The fact that the opening threshold of the thresholded valve is greater than 1.5 bar (and preferably greater than or equal to 2 bar) makes it possible to guarantee that the container is well pressed against the bladder and the cushion. This pressing is necessary to allow such an injector to control:
- the quantity of contrast product injected into the patient during an administration phase,
- the quantity of contrast product introduced into the container during a filling phase.

In effect, during an administration phase, the principle of operation of such an injector is as follows: the bladder is filled with hydraulic fluid such that the walls of the container are pressed against the walls of the cushion and of the bladder. When the walls of the bladder and of the cushion are pressed against the container, the introduction of a given quantity of hydraulic fluid into the bladder induces the expulsion of the same quantity of contrast product out of the container. For example, one milliliter of non-compressible fluid introduced into the bladder mechanically "drives" one milliliter of contrast product out of the container 3. Thus, once the walls of the container are pressed against the bladder and the cushion, it is possible to accurately control the quantity of product injected into the patient by measuring the quantity of hydraulic fluid introduced into the bladder.

During a filling phase, the principle of operation of such an injector is as follows: the bladder is filled with hydraulic fluid such that the walls of the container are pressed against the cushion and the bladder. The introduction of contrast product into the container induces an increase in its volume which tends to apply a thrust force on the cushion and the bladder. This force induces the expulsion of hydraulic fluid out of the bladder. More specifically, when the walls of the container are pressed against the bladder and the cushion, the introduction of a given quantity of contrast product into the container induces the expulsion of the same quantity of hydraulic fluid out of the bladder. Thus, once the walls of the container are pressed against the bladder and the cushion, it is possible to accurately control the quantity of contrast product introduced into the container by measuring the quantity of hydraulic fluid expelled from the bladder.

The fact that the opening threshold of the threshold valve is greater than 1.5 bar (and preferably greater than or equal to 2 bar) makes it possible to guarantee that the container 3 is well pressed onto the bladder and the cushion even before the slightest flow of contrast product out of the container, the flow of contrast product out of the container requiring a minimum pressure of 1.5 bar in the container.

Filling Line

The filling line 2 comprises a nozzle or upstream filling line section 21 upstream of the coupling interface 26 and a nozzle or downstream filling line section 23 downstream of the coupling interface 26. An upstream connector 100 is disposed between and couples the nozzle 21 with the coupling interface 26, while a downstream connector 102 is disposed between and couples the nozzle 23 with the coupling interface 26.

In a variant embodiment, the length of the nozzle 21 upstream of the coupling interface 26 is between 400 and 800 millimeters in order to limit the head losses between the coupling interface 26 and the feed source 4 during the suction of the fluid for the filling of the container 3.

Moreover, the internal diameter of the nozzle 21 upstream of the coupling interface 26 can be greater than the internal diameter of the downstream tubular part 11 of the injection line 1. In particular, the internal diameter of the nozzle 21 upstream of the pumping unit 22 can be between 3 and 6 millimeters.

By maximizing the internal diameter of the nozzle 21 upstream of the coupling interface 26, it becomes possible to limit the head losses between the primary feed source 4 and the coupling interface 26 during the suction of the fluid for the filling of the container 3.

Furthermore, the hardness of the nozzle 21 upstream of the coupling interface 26 can be greater than the hardness of the nozzle 23 downstream of the coupling interface 26. In particular, the hardness of the nozzle 21 upstream of the coupling interface 26 can be equal to or greater than 70 ShA. By having a nozzle 21 of a hardness equal to or greater than 70 ShA, it becomes possible to avoid any collapsing thereof during the suction of the fluid for the filling of the container 3. Preferably, the hardness of the nozzle is chosen to be less than 90 ShA to facilitate its winding during packaging and facilitate its handling by the operator during installation on the injector.

Advantageously, the hardness of the nozzle 23 downstream of the coupling interface 26 can be chosen to be less than the hardness of the downstream tubular part 11 of the injection line 1. Notably, the Shore A hardness of the nozzle 23 downstream of the coupling interface 26 can be between 60 and 80 ShA.

The fact that the hardness of the nozzle 23 is less than or equal to 80 ShA makes is possible for the filling line 2 to absorb any pulsing generated by the pumping unit 22 in order to limit the risks of overpressure in the assembly for medical use, overpressure potentially inducing a leak of product to the patient through the high-thresholded non-return valve 13 of the injection line 1. The fact that the hardness of the nozzle 23 is greater than or equal to 60 ShA makes it possible to limit the risk of breaking of this nozzle 23 under the effect of the pressure.

As a variant, the diameter of the nozzle 23 downstream of the coupling interface 26 can be chosen to be greater than the diameter of the downstream tubular part 11 of the injection line 1. Notably, the diameter of the nozzle 23 downstream of the coupling interface 26 can be between 3 and 6 millimeters. Here again, this makes it possible to absorb pulsing generated by the pumping unit 22.

The filling line 2 can also comprise a non-return valve 25 allowing liquid to pass in a single direction, namely from the primary feed source 4 to the container 3. The presence of a non-return valve 25 makes it possible to isolate the filling line 2 once the filling phase is finished, and do so without requiring any manipulation on the part of the user prior to the implementation of the phase of administration of the product to the patient.

The filling line 2 can comprise a bubble trap 24—such as a drop-count chamber—between the primary feed source 4 and the container 3. This bubble trap 24 makes it possible to drive out the air between the primary feed source 4 and the container 3.

Principle of Operation of the Assembly

The principle of operation of the assembly for medical use described above is as follows: during the implementation of an operation to inject product into a patient, the user takes the assembly for medical use out of its packaging. He or she connects:

the free end of the filling line 2 to the primary feed source 4, and the free end of the injection line 1 to the patient after having bled the injection line 1.

When the container 3 is incorporated in the assembly, there is no need for any step of connecting the latter, which limits the risks of contamination of the assembly during its installation.

The user then implements the filling phase. The pumping unit 22 is actuated to fill the container 3 with the product to be injected. The product to be injected is displaced between the primary feed source 4 and the container 3. The non-return valve 13 with high triggering threshold prevents the product from passing into the downstream tubular part 11 of the injection line 1 in order to avoid any risk of untimely release of product to be injected toward the free end of the injection line 1 during the filling phase.

The container 3 is filled with product to be injected. When the quantity of product contained in the container 3 is sufficient, the user stops the filling phase to implement the phase of administration of the product to the patient by having previously bled the air originally contained in the filling 2 and injection 1 lines.

The container 3 is then pressurized—for example by using a pocket injector or a thrust syringe device—to induce the displacement of the product between the container 3 and the patient.

The non-return valve 25 of the filling line 2 prevents the product from passing between the container 3 and the primary feed source 4. The product passes through the injection pipe 15 and enters into the patient. When a sufficient quantity of product has been administered to the patient, the administration phase is stopped either automatically, or by an actuation on the part of the user.

Thus, the assembly described above makes it possible to perform rapid transfers of liquid or viscous product between:

a primary feed source 4 and a container 3 on the one hand, and the container 3 and a patient on the other hand, while limiting the risks of contamination by the user.

The reader will have understood that numerous modifications can be made to the assembly for medical use without materially departing from the novel teachings and advantages described herein.

Consequently, all modifications of this type are intended to be incorporated within the scope of the attached claims.

The invention claimed is:

1. An assembly for use in a patient injection, comprising:
a container;
an injection flowpath that is exterior of said container and that comprises an upstream injection line tubular part exterior of said container, a three-way connector exterior of said container, a downstream injection line tubular part exterior of said container, and a first one-way valve exterior of said container, wherein said upstream injection line tubular part is between a first port of said three-way connector and said container, wherein said downstream injection line tubular part is between a second port of said three-way connector and a patient when fluidly connected with said assembly and where said first one-way valve allows flow in only a single direction between said container and this patient, wherein said container, said upstream injection line tubular part, said three-way connector, and said downstream injection line tubular part are separate parts from one another; and a filling flowpath that intersects said injection flowpath exteriorly of said container and that comprises an upstream filling line tubular section, an upstream connector, a pump coupling section intended for engagement by a pumping unit, a downstream connector, a downstream filling line tubular section, a second one-way valve, said three-way connector, and said upstream injection line tubular part, wherein said upstream filling line tubular section extends from said upstream connector and toward a feed source when fluidly connected with said assembly, wherein said pump coupling section consists of a flexible pipe and said flexible pipe extends from said upstream connector to said downstream connector, wherein said downstream filling line tubular section extends from said downstream connector and toward a third port of said three-way connector, wherein said second one-way valve only allows flow in a single direction between said pump coupling section and said container, wherein said upstream filling line section, said upstream connector, said pump coupling section, said downstream connector, and said downstream filling line section are separate parts from one another with said upstream connector coupling said upstream filling line section to said pump coupling section and with said downstream connector coupling said downstream filling line section to said pump coupling section;

wherein fluid being loaded into said container flows in the following ordered sequence for said assembly: 1) said upstream filling line tubular section; 2) said upstream connector; 3) said pump coupling section; 4) said downstream connector; 5) said downstream filling line tubular section; 6) a flowpath extending from said third port of said three-way connector to said first port of said three-way connector; and 7) said upstream injection line tubular part;

wherein fluid being directed from said container flows in the following ordered sequence for said assembly: 1) said upstream injection line tubular part; 2) a flowpath extending from said first port of said three-way connector to said second port of said three-way connector; and 3) said downstream injection line tubular part;

wherein fluid flows through said upstream injection line tubular part in a first direction during a fluid loading operation where fluid is directed into said container, and wherein fluid flows through said upstream injection line tubular part in a second direction, opposite of said first direction, during an injection operation where fluid is directed out of said container; and wherein a hardness of said upstream filling line tubular section that extends from said upstream connector is different than both a hardness of said pump coupling section and a hardness of said downstream filling line tubular section that extends from said downstream connector.

2. The assembly of claim 1, wherein an inner diameter of said upstream filling line tubular section is greater than an inner diameter of said downstream injection line tubular part.

3. The assembly of claim 2, wherein said hardness of said downstream filling line tubular section is less than a hardness of said downstream injection line tubular part.

4. The assembly of claim 1, wherein said hardness of said downstream filling line tubular section is less than a hardness of said downstream injection line tubular part.

5. The assembly of claim 1, wherein said filling flowpath further comprises a bubble trap, wherein said upstream filling line tubular section is located between said pump coupling section and said bubble trap.

6. The assembly of claim 1, further comprising a non-removable connection between said container and said upstream injection line tubular part.

7. The assembly of claim 1, further comprising a pumping unit that engages said pump coupling section.

8. The assembly of claim 1, further comprising an injector, wherein said injector presses against said container as fluid is being loaded into said container from a feed source from which said filling flowpath extends.

9. The assembly of claim 1, wherein said hardness of said upstream filling line tubular section is greater than said hardness of said downstream filling line tubular section, and wherein said hardness of said downstream filling line tubular section is less than a hardness of said downstream injection line tubular part.

10. The assembly of claim 9, wherein said hardness of said pump coupling section is less than said hardness of said upstream filling line tubular section.

11. The assembly of claim 10, wherein an inner diameter of said upstream filling line tubular section is greater than an inner diameter of said downstream injection line tubular part.

12. The assembly of claim 1, wherein said hardness of said pump coupling section is less than said hardness of said upstream filling line tubular section.

13. The assembly of claim 1, wherein said hardness of said upstream filling line tubular section is greater than said hardness of said downstream filling line tubular section.

* * * * *